US 8,784,460 B2

United States Patent
Kriksunov et al.

(10) Patent No.: US 8,784,460 B2
(45) Date of Patent: Jul. 22, 2014

(54) MICROCURRENT DEVICE WITH A SENSORY CUE

(75) Inventors: Leo B. Kriksunov, Glenside, PA (US); Aliya Z. Omer, Houston, TX (US); Edward Roche, Paoli, PA (US); Joshua Ghaim, Princeton, NJ (US); Naomi Furgiuele, Doylestown, PA (US)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

(21) Appl. No.: 13/611,079

(22) Filed: Sep. 12, 2012

(65) Prior Publication Data

US 2013/0013028 A1    Jan. 10, 2013

Related U.S. Application Data

(62) Division of application No. 12/261,410, filed on Oct. 30, 2008, now Pat. No. 8,290,581.

(60) Provisional application No. 60/983,792, filed on Oct. 30, 2007.

(51) Int. Cl.
  *A61N 1/00*    (2006.01)
  *A61H 1/00*    (2006.01)
  *A61B 5/04*    (2006.01)

(52) U.S. Cl.
  USPC ............... 607/1; 607/2; 607/3; 607/7; 601/5; 600/372

(58) Field of Classification Search
  USPC .................... 607/1–3, 7; 601/5; 600/372
  See application file for complete search history.

(56) References Cited

U.S. PATENT DOCUMENTS

| | | |
|---|---|---|
| 4,121,594 A | 10/1978 | Miller et al. |
| 5,042,975 A | 8/1991 | Chien et al. |
| 5,162,043 A | 11/1992 | Lew et al. |
| 5,354,321 A | 10/1994 | Berger |
| 5,423,874 A | 6/1995 | D'Alerta |
| 5,851,223 A | 12/1998 | Liss et al. |
| 5,897,522 A | 4/1999 | Nitzan |
| 6,175,763 B1 | 1/2001 | Sorenson et al. |
| 6,275,372 B1 | 8/2001 | Vasallo et al. |
| 6,408,211 B1 | 6/2002 | Powell |
| 6,552,895 B1 | 4/2003 | Vassallo et al. |
| 6,606,519 B2 | 8/2003 | Powell |
| 7,463,917 B2 | 12/2008 | Martinez |
| 2003/0059673 A1 | 3/2003 | Langan et al. |
| 2003/0233137 A1 | 12/2003 | Paul, Jr. |

(Continued)

FOREIGN PATENT DOCUMENTS

WO    WO 2005/119610 A1    12/2005

OTHER PUBLICATIONS

Becker, R.O., "The Ticklish Gene—A Surprise in the Blood", The Body Electric. New York: William Morrow and Co., 1985, pp. 135-141.

(Continued)

*Primary Examiner* — Nicole F Lavert
(74) *Attorney, Agent, or Firm* — Victor Tsu

(57) ABSTRACT

The present invention is directed to an apparatus that includes a microcurrent delivery device portion and at least one independent sensory cue delivery means. The independent sensory cue delivery means can provide an independent sensory cue selected from the group consisting of vibration, heat, cool, skin irritation, tingling, fragrance or auditory.

3 Claims, 5 Drawing Sheets

(56) References Cited

U.S. PATENT DOCUMENTS

| | | |
|---|---|---|
| 2004/0138712 A1 | 7/2004 | Tamarkin et al. |
| 2005/0043655 A1* | 2/2005 | Schenck .................. 601/15 |
| 2005/0125040 A1 | 6/2005 | Lathrop |

OTHER PUBLICATIONS

Cheng, Ngok, M.D. et al., "The Effects of Electric Currents on ATP Generation, Protein Synthesis, and Membrane Transport in Rat Skin", Clinical Orthopaedics and Related Research, 1982, pp. 264-272, vol. 171.

Illingworth, Cynthia M. et al., "Measurements of electrical currents emerging during the regeneration of amputated fingertips in children", Clinical Phys. Physiol. Meas., 1980, pp. 87-89, vol. 1.

Kulig, K. et al., "The Effects of Microcurrent Stimulation on CPK and Delayed Onset Muscle Soreness", Physical Therapy, Jun. 1991, pp. S115-S116, vol. 71, No. 6 (Suppl).

LeDoux, Mark S. MD et al., "Spinal Cord Stimulation for the Failed Back Syndrome", Spine, Feb. 1993, pp. 191-194, 18(2), Abstract.

Mercola, Joseph M. Do et al., "The Basis for Microcurrent Electrical Therapy in Conventional Medical Practice", Journal of Advancement in Medicine, (1995), pp. 107-120, vol. 8, No. 2.

Neumann, V., "Editorials—Electrotherapy", British Journal of Rheumatology, 1993, pp. 1-3, vol. 32.

Nordenstrom, B., Biological Closed Electric Circuits: Clinical, Experimental, and Theoretical Evidence for an Additional Circulatory System. Nordic Medical Publications. Uppsala. 1983, pp. 1-10.

North, Richard B. M.D. et al., "Spinal Cord Stimulation for Chronic, Intractable Pain: Experience over Two Decades", Neurosurgery, 1998, pp. 384-395, vol. 32(3).

Reich, Jonathan D. M.S. et al., Electrical Stimulation of Skin, Int. J. Derm., Aug. 1990, pp. 395-400, vol. 29, No. 6.

Stanish, William D. MD et al., "New concepts of rehabilitation following anterior cruciate reconstruction", Clinics in Sports Medicine, Jan. 1993, pp. 25-58, vol. 12, No. 1.

Stanish, William D. MD et al., "The Use of Electricity in Ligament and Tendon Repair", Physician and Sportsmedicine, Aug. 1985, pp. 109-116, vol. 13, No. 8.

Vodovnik, L. et al., "Treatment of chronic wounds by means of electric and electromagnetic fields", Part 1 Literature review, Medical & Biological Engineering & Computing, May 1992, pp. 257-266, vol. 30.

Windsor, Robert E. et al., "Electrical Stimulation in Clinical Practice", Physician & Sportsmedicine, Feb. 1993, pp. 85-93, vol. 21, No. 2.

* cited by examiner

# MICROCURRENT DEVICE WITH A SENSORY CUE

RELATED APPLICATION

This application claims priority to U.S. application Ser. No. 12/261,410, filed on Oct. 30, 2008, and to U.S. application Ser. No. 60/983,792 filed Oct. 30, 2007, the entire contents of which are incorporated herein by reference.

CROSS REFERENCE TO RELATED APPLICATIONS

This application claims priority of the benefits of the filing of U.S. Provisional Application Ser. No. 60/983,792, filed Oct. 30, 2007. The complete disclosures of the aforementioned related U.S. patent application is/are hereby incorporated herein by reference for all purposes.

BACKGROUND OF THE INVENTION

During the past decade, microcurrent therapy has been shown to be effective in pain control. Microcurrent electrical therapy or microcurrent therapy, first coined by Mercola and Kirsch in 1995, describes a new form of electro-medical intervention using biocompatible waveforms and uses current in the microampere range, 1000 times less than that of transcutaneous electrical nerve stimulation (i.e. TENS) and below the sensation threshold.

Some of the early thinking relating to energy treatments, as shown in studies reviewed by North (9) and by Neumann (11), was that if some electricity is good perhaps more is better. This concept, however, was later challenged by investigators such as Becker and Nordenstrom, who wrote "The Body Electric" (2) and "Biological Closed Electric Circuits: Clinical, Experimental, and Theoretical Evidence for an Additional Circulatory System"(12), respectively.

Microcurrent stimulators have been used since early 1980s, but only recent technological advances in electronics and power sources have allowed more advanced devices that are wearable and portable.

Studies by Illingsworth (13) and Vodovnick (5) have found microcurrent reduces inflammation, edema and swelling, increases range of motion, strength and muscle relaxation, and accelerates wound healing. These current therapies have also been found by Stanish (6)) and Stanish and Lai (7) to be effective in soft tissue injuries, such as sprains and has also been proven useful in preventing the delayed muscle soreness that is common after heavy exercise. These current therapies have been used to control failed back syndrome as referenced by North (9) and shown by LeDoux (10) and for arthritis according to Neumann (11). There is a growing body of research showing that MCT is capable of doing more than just control pain, such as accelerating and even inducing healing. It has also been proven useful in preventing the delayed muscle soreness that is common after heavy exercise as shown by Kulig (8)

William Stanish, a physician for the Canadian Olympic Team demonstrated that implanted electrodes delivering 10-20 microamps of electrical current hastened the recovery from ruptured ligaments and tendons. Using microcurrent stimulation, Dr. Stanish shortened the normal 18 month recovery period to only 6 months, as reported in Physician and Sportsmedicine (6).

Physiological effects of MCT, which has also been called "bio-stimulation" or "bio-electric therapy" because of its ability to stimulate cellular physiology and growth was first demonstrated in a landmark study (3) by Cheng et al. in 1982. Using varying levels of electrical current on in-vitro slices of rat skin, the investigators showed up to 500% increase in ATP generation as well as increase in amino acid transport and protein synthesis in specimens treated with currents below 600 microamps, compared to that of the control group. The most significant finding of this study was specimens stimulated at levels above 1 milliamp (TENS levels) showed depressed levels of amino acid synthesis and ATP generation, often significantly lower than controls. This was strong evidence of the superiority of microcurrents over milliamp currents for stimulating cellular healing.

Becker has shown that trauma will affect the electrical potential of cells in damaged tissues. Initially, the site of an injury has much higher resistance than the surrounding tissue. Basic physics dictates that electricity will always take the path of least resistance; therefore, endogenous electrical current will travel around the site of injury. This results in decreased electrical conductance through the injured area and decreased cellular capacitance, leading to impairment of the healing process as shown by Windsor (14) in Physician and Sportsmedicine.

Pain, heat, swelling and redness are the characteristics of inflamed tissues. It has been reported that electricity flows more readily through inflammatory fluids and correct application of microcurrent to an injured site is believed to enhance the endogenous current flow, thus allowing cells in the traumatized area to regain their capacitance. A study has reported on a link between the effects of microcurrent to enhanced cellular activities such as protein synthesis and ATP generation and is believed to be the key mechanism of action for microcurrent therapy. See Cheng (3).

Microcurrent is an energy-based therapy, defined as the application of electrical current to the external parts of the body, typically on the skin, and applied as a current in a range of 20-500 microamperes. A typical microcurrent apparatus is composed of a patch and with an accompanying power supply source with positive and negative energy delivery electrodes leads attached from the power supply source s. While microcurrent is applied to external parts such as the skin, it is used for treatment of pain in both muscle and joint tissue and may be applied in various configurations to the elbows, knees, back, shoulder or neck. Generally, microcurrent is supplied through a device and is differentiated from other electrotherapy devices in that the amount of current which is supplied is less than the amount used in transcutaneous electrical nerve stimulation (i.e. TENS).

TENS devices are known for delivering electromagnetic stimulation as described in U.S. Pat. No. 4,121,594; "Transcutaneous Electrical Nerve Stimulator", Miller et. al; and U.S. Pat. No. 5,423,874; "Patch for Applying Pain Reducing Energy to the Body" D'Alerta et. al. A microcurrent therapy device can be defined as one which delivers a DC current of less than one milliampere, typically in the range of 20-500 microamperes; whereas TENS devices deliver DC current in a range greater than 1 milliampere; typically at 5 to 20 milliamperes. Devices for use in the application of therapeutic microcurrent is described in U.S. Pat. No. 5,354,321.

Microcurrent devices are generally applied for a long period of time, which includes wearing the device for a time longer than that used for TENS devices. In addition, one major characteristic inherent in microcurrent devices is that the current which is supplied is transmitted below the sensory threshold of the user, and in turn, is not "felt" immediately upon application of the device. Pain relief is achieved over an extended period of time while wearing the device and it is further believed to have longer term effects beyond stimulation.

Since the microcurrent energy is not sensed by the user, it is advantageous to let the user know that the device is working and delivering the appropriate therapeutic dose of microcurrent through the device. A solution to this has been proposed in U.S. Pat. No. 6,408,211; "Microcurrent Therapy Device" is the addition of a visual indicator, such as LED, to the surface of the device, which indicates to the user that the device is on and working. One issue with this approach is that most users do not associate LED indication in conjunction with pain relief or energy delivery, and in essence does not act to deliver any additional cue to the user that the device is actually functioning in a temporary pain relieving capacity. In addition, the user must remember to periodically examine the device to see whether or not the LED is on. The requirement for a visual check could be very difficult if the site of pain is out of the visual capacity of the user (i.e. low back pain) and when the device is worn under the user's clothing. Additionally, a further shortcoming is that the LED signal is not detectable to a user while sleeping. Further, the proposed solution does not provide a signal of dysfunction. For example, if a user is moving or if the friction from clothing disconnects the device, contact uniformity is disrupted, and there is no signal to communicate the disruption to the user.

U.S. Pat. No. 6,606,519 describes a microcurrent therapy device that includes various components, including a coin battery and conductive pads, in a stack configuration.

Published U.S. Patent Application 20040138712 describes a combination stimulating and exothermic heating device and method of use. This application describes types of eletrostimulation such as TENS which actually provides a therapeutic treatment to the user in combination with an exothermic heating therapeutic component, which is a type of heat which is difficult to control and deliver in a precise or timed manner.

Published PCT Application WO 2005/119610 describes an electrocommunication unit which is used for delivering a series of electrical pulses to the skin to serve as a reminder or wake-up device.

U.S. Pat. No. 6,175,763 describes an electrotransport system for delivering active drugs through the skin and for delivering a tactile signal to the skin of a patient. The system includes a sensor connected to the system for sensing an event or condition associated with the operation of the system. The method includes monitoring a condition or event associated with the operation of the system and generating a tactile signal, which signal can be felt by the patient wearing the system, when the condition or event occurs.

The following references and patents/patent applications are discussed above are incorporated herein by reference:

1. Mercola, J. M., Kirsch, D. L. (1995). The basis for microcurrent electrical therapy in conventional medical practice. Journal of Advancement in Medicine, 8 (2), 107-120.

2. Becker R O. The Body Electric. New York: William Morrow and Co., 1985.

3. Cheng N., et al. The effects of electric currents on ATP generation, protein synthesis and membrane transport in rat skin. Clin. Orthop. 1982; 171:264-272.

4. Reich J D and Tarjan P P. Electrical stimulation of skin. Int. J. Derm. 1990; 29:395-400.

5. Vodovnik L and Karba R. Treatment of chronic wounds by means of electric and electromagnetic fields. A literature review. Med Biol Engineer Comput. 1992; 30:257-266.

6. Stanish W D, et al. The use of electricity in ligament and tendon repair. Physician and Sportsmedicine. 1985; 13:109-116.

7. Stanish W D and Lai A. New concepts of rehabilitation following anterior cruciate reconstruction. Clin. Sports Med. 1993; January; 12(1):25-58.

8. Kulig K, et al. The effect of microcurrent stimulation on CPK and delayed onset muscle soreness. Physical Therapy. 1991; 71:6(suppl).

9. North R B, et al. Spinal cord stimulation for chronic, intractable pain: experience over two decades. Neurosurgery. 1998; 32:384-395.

10. LeDoux M S and Langford K H. Spinal cord stimulation for the failed back syndrome. Spine. 1993; 18:191-194.

11. Neumann V. Electrotherapy. Br J Rheumatol. 1993; 32:1-3.

12. Nordenstrom, B. Biological Closed Electric Circuits: Clinical, Experimental, and Theoretical Evidence for an Additional Circulatory System. Nordic medical Publications. Uppsala. 1983.

13. Illingsworth C M and Barker A T. Measurements of electrical currents emerging during the regeneration of amputated fingertips in children. Clinical Phys. Physiol. Meas. 1980; 1:87-89.

14. Windsor R E, et al. Electrical Stimulation in Clinical Practice. Physician & Sportsmedicine. 1993; 21:85-93.

SUMMARY OF THE INVENTION

The invention disclosed herein is directed to a combinatorial microcurrent device which provides an independent sensory cue to a user, that is the cue is activated upon application of the device and does not require any action on the part of the consumer to initiate or receive the sensory cue. The independent sensory cue in this invention is associated with device initiation to communicate function and can also be used to communicate a device operational dysfunction. For example, in a microcurrent device, contact uniformity is essential to ensure that electrical current flows through the barrier membrane to effect positive physiological effects. If contact is lost, a sensory cue can alert the user that effective treatment has been disrupted.

The cue or cues may be delivered in the form of energy including, but not limited to such as vibration, heat, cooling, detectable electrical pulses, ultrasound, auditory stimulus, or alternatively, via chemical cues such as fragrances, heating sensates, heating analgesics and cooling sensates. In addition, a temperature control feature can be integrated into the device through the use of phase change materials or other means of regulating temperature through exothermic reduction-oxidation reactions or by other means of electrical heating.

The independent sensory cues described above can be coupled with other forms of observational feedback cues, such as low powered LCD screen. The independent sensory cues, such as the heating, cooling and chemical sensates, can also separately function as an immediate signal to the user and in a potential dual function to provide an immediate relief of pain.

In another embodiment, the sensory cue is provided permanently or periodically once the device is actuated as reminder and feedback to consumer, independent of the operational status of the microcurrent treatment device.

BRIEF DETAILED DESCRIPTION OF THE FIGURES

DETAILED DESCRIPTION OF THE INVENTION

Microcurrent is an energy-based therapy, defined as the application of electrical current to the external parts of the body, typically on the skin, and applied as a current in a range of 20-500 microamperes. A conventional microcurrent apparatus is composed of a patch and a power supply source with positive and negative energy delivery electrodes leads attached from the power supply source. While microcurrent is applied to external parts such as the skin, it is used for treatment of pain in both muscle and joint tissue and may be applied in various configurations to the elbows, knees, back, shoulder or neck. Microcurrent therapy is differentiated from other electrotherapy devices in that the amount of current that is supplied is less than the amount used in transcutaneous electrical nerve stimulation (i.e. TENS).

Figure 1A:
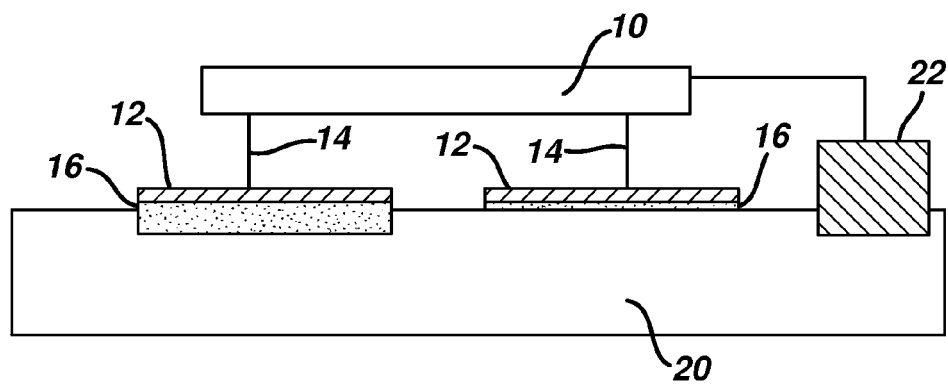
FIG. 1A illustrates a wired embodiment of the present invention.
Figure 1B:
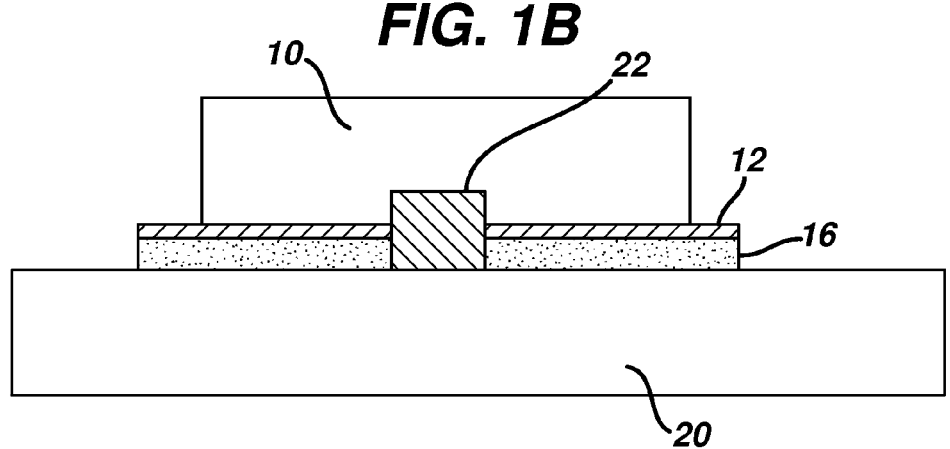
FIG. 1B illustrates a wireless embodiment of the present invention.

FIGS. 1A and 1B illustrate wired and integrated wireless embodiments of electrostimulation devices or micro-current therapy devices of the present invention. A therapy device, in one embodiment, includes a current generator 10 capable of generating high voltage pulses for electric feedback intermittently through electrode pads 12. Conductive lines 14 in the wired embodiment provide an electrical connection from the current generator 10 to electrode pads 12. In one embodiment, the high voltage pulses are supplied through the same electrode pads 12 that are used to deliver microcurrent therapeutic current. In another embodiment (not shown), optional additional electrode pads are provided for delivering high voltage pulses in addition to the electrodes 12 that provide microcurrent therapeutic current.

Electrode pads 12 can be provided with an optional carrier 16 that, when the therapy device is in use, are positioned between the exterior surface 20 body of the patient electrode pads 12. Thermal feedback or sensory cue means 22, as exemplified by electrically heated member such as resistive heater, can be positioned in contact with the patient's body. In one embodiment, a space or a gap can be provided between electrode pads 12 as shown in FIG. 1A. In another embodiment, there is no gap or space between thermal feedback or sensory cue means 22 and electrode pads 12 as exemplified in FIG. 1B. In yet another embodiment, thermal feedback or sensory cue means 22 are temporarily affixed to the patient's body through a hydrogel or adhesive media or through a non-adhesive thermally conductive media such as gels, polymers, metals, or composites. In another embodiment, thermal feedback or sensory cue means 22 are positioned behind the electrode pads and supply thermal sensory cues directly through electrode pads.

The device disclosed herein is used to treat pain, and other inflammatory conditions including, but not limited to generalized localized pain, chronic pain, joint pain, muscle pain, back pain, rheumatic pain, arthritis, wound treatment, osteoarthritis and combinations thereof. In one embodiment the sensory cue is delivered in a continuous and uninterrupted manner. In another embodiment, the sensory cue is delivered in an interrupted or periodic manner, e.g. in a periodic manner (i.e. the start and end of treatment.).

"Independent sensory cues", as described herein, shall refer to all cues that are activated upon application of the device and do not require action by the user to recognize the cue. Examples of suitable independent sensory cues include, but are not limited to vibration, heating, cooling, detectable electrical pulses, ultrasound, auditory cues or alternatively, via chemical cues such as fragrances, heating sensates, heating analgesics, and cooling sensates. In one embodiment the sensory cue is sensed by the user even when the device is worn under the user's clothing and is not directly visible to the user. In one embodiment the sensory cue is delivered to indicate to the user that the device is not working.

Feedback or sensory cue means shown in FIGS. 1A and 1B can be vibratory, electric, thermal, and sensate sensory cue means. Referring to FIG. 1A, an embodiment of a wired electrostimulation device or micro-current therapy device is shown. Electrode pads 12 having optional carrier 16, such as a hydrogel coatings, are positioned on the exterior surface 20 of the body of the patient. Feedback or sensory cue means 22 are also positioned in contact with the body of the patient. Electrode pads 12 and sensory cue means 22 are connected via conductive lines 14 to the current generator 10 of the device, which current generator contains a power supply, electronics and controls. (Comments need more)

Referring to FIG. 1B, an embodiment of an integrated or wireless electrostimulation device or micro-current therapy device is shown. Electrode pads 12 having optional hydrogel coating 16 are positioned on the exterior surface 20 of the body of the patient. Feedback or sensory cue means 22 are also positioned in contact with the exterior surface 20 of the body of the patient. Electrode pads and sensory cue means 22 are integrated within the housing 10 of the device also containing power supply, electronics and controls within said body.

The present invention relates to a device for the delivery of electricity, in the preferred form, microcurrent, (e.g., to induce a desirable biological response) into a barrier membrane or skin and is coupled with a spontaneous/independent consumer signal. In one embodiment, the device of the present invention is a self-contained device that provides at least one independent sensory cue having at least one pair of conductive electrodes 12 wherein each electrode 12 is contained in a separated compartment or carrier and is affixed to the skin with electric insulation between the pair of electrodes 12 so that all of the electric current generated by the device travels through the skin and underlying tissue to complete the electric circuit. A power source can be connected to the pair of electrodes 12. Alternatively, the two conductive electrodes 12 can be formed using a pair of two dissimilar conductive electrodes 12 in electric communication as a power source.

In one embodiment, the absence or low value of the current flowing through the patients body is detected and appropriate sensory cue is provided to the patient by either activating or de-activating the feedback mechanism in the device. The current flowing through the body is measured by an amp meter; when the measured current flow falls below a pre-set value, e.g. below 25 microamps, below 10 microamps or other pre-set value, an independent and optionally an observational sensory cue is delivered to the patient. Upon a reading below or at a set point on the amp meter, a signal would be transmitted to the feedback means or sensory cue means to activate such means.

The microcurrent therapy device of the present invention can optionally include a carrier 16 that contacts and adheres to the exterior surface 20 of a person's body (e.g., a skin contacting surface). In one embodiment, carrier 16 is a hydrogel.

In one embodiment, the device delivers an independent and optionally an observational cue to the user upon application of carrier 16 to electrode pads 12. In one embodiment, the device delivers the independent and optionally an observational cue only when placed on the skin. In one embodiment the device is activated including the delivery of the sensory cue upon connection to the power source or activation of a switch which connects to the power source.

Vibratory Cue Means

In one embodiment, vibration is combined in a microcurrent device and supplied as the independent sensory cue to the user. Vibration can be added as an initial burst when the device is applied at the barrier membrane, like the skin, or as a periodic pulse at a specified time interval. In one embodiment, the vibration is administered at time intervals of every 60 minutes, e.g. every 30 minutes, e.g. every 10 minutes, e.g. every 5 minutes, e.g. every 1 minute, e.g. every 30 seconds or time periods that correlate with treatment start and end points. Vibratory energy can be supplied in a device using various mechanisms including but not limited to delivery via electromagnetic vibratory mechanism, piezo-ceramics or piezo-polymer based vibratory mechanism, or an electric micro-motor, including micro-motor having a rotor with an offset center of mass, or other vibratory mechanism known in the art. The intensity and frequency of vibration is selected so as to provide a detectable sensation to the user of the device.

In one embodiment, a vibration with the frequency of from about 1 Hz to about 50 KHz is utilized and with amplitude of from 1 micron to 5 mm peak-to-peak or a singular event, rather than multitude of vibrations. The vibratory energy is sensed by the user's skin and is transferred to the skin entirely directly to the skin or indirectly through the device.

In one embodiment, a vibratory cue means in direct contact with the patient's body and thus directly transfers the vibratory energy to the patient's body. In another embodiment, the vibratory sensation is transmitted to the patient though an air gap. In yet another embodiment, the vibratory sensation is transmitted to the device or components thereof.

Piezo-ceramics based vibratory mechanisms utilize piezo-ceramics components as known in the art, such as PZT (lead-zirconium-titanate) ceramics, typically coupled to one or two metal or polymer components to form a uni-morph or a bi-morph vibratory element. Upon application of alternating voltage at a frequency close to the resonant frequency of the vibratory element assembly, the vibratory element develops high amplitude vibratory oscillations.

Figure 1C:
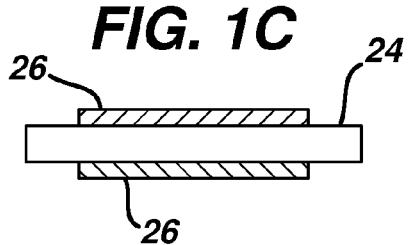
FIG. 1C illustrates a vibration sensory device of the present invention.

Electro-magnetic vibratory mechanisms are known in the art and typically utilize an electro-magnetic coil that is energized with an alternating current to generate an alternating magnetic field, which in turn results in oscillations of a metallic component. Referring to FIG. 1C, an embodiment of a vibratory sensory cue means is shown. A bi-morph piezo vibratory element is shown that has a piezo ceramic disk 20 and two metal members 26 that are attached to the disk 20 on both sides. Application of electric voltage at a frequency close to the resonant frequency of the assembly results in high amplitude vibrations of the assembly, which then serves as a vibratory sensory cue.

In another embodiment the vibratory cue is provided by a vibratory mechanism based on a micro-motor with a rotating weight inside the vibratory mechanism, wherein the weight is mounted off-balance.

Electric Impulse Cue Means

The electro stimulation used as a sensory cue or feedback to the patient is applied between sensory threshold and the motor threshold so that the patient can feel the sensation, but the sensation does not cause muscle contraction or only minor muscle contraction. Further, the stimulation is applied at a level, which does not cause uncomfortable or painful feeling. The level of stimulation necessary to achieve these objectives varies from person to person. Literature data on the sensory threshold, motor threshold, and pain threshold are also variable. In addition, the sensory threshold, motor threshold, and the pain threshold are a function of the surface area of the stimulation. Additional variables that affect the thresholds are current density, region of the body, the length of the electric impulse and of the frequency of impulses. Higher current density will typically result in stronger sensation.

Figure 1D:
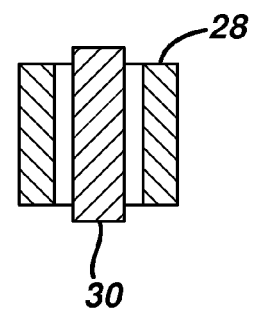
FIG. 1D illustrates an alternative vibration sensory device of the present invention.

Referring to FIG. 1D, an embodiment is shown of an electromagnetic vibratory sensory cue means. An electromagnet, such as induction coil 28, is energized with alternating current and interacts with a metal core 30 made, for example, of iron. Metal core 30 vibrates as a result of this interaction and creates an independent vibratory sensory cue. Based on the Strength-duration curves (Electrotherapy Explained, Principles and Practice, Val Robertson et al., Elsevier 2006, page 61), for a pulse duration of about 10 microseconds, the sensory threshold is around 50V, the motor threshold is around 130V, and the pain tolerance limit is at about 250V. For longer impulses, all three thresholds are significantly lower, with sensory threshold being at only a few volts for 100 microsecond impulses.

Figure 3A:
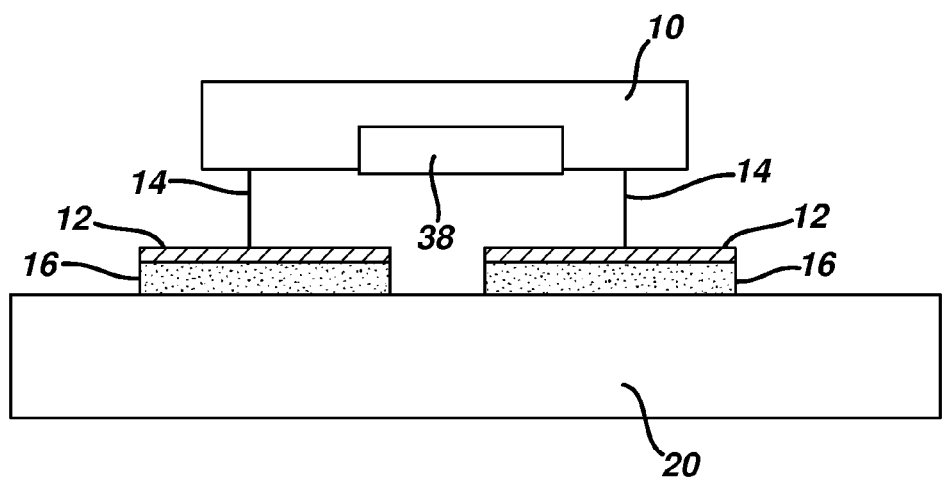
FIG. 3A illustrates a chemical sensory embodiment of the present invention.
Figure 3B:
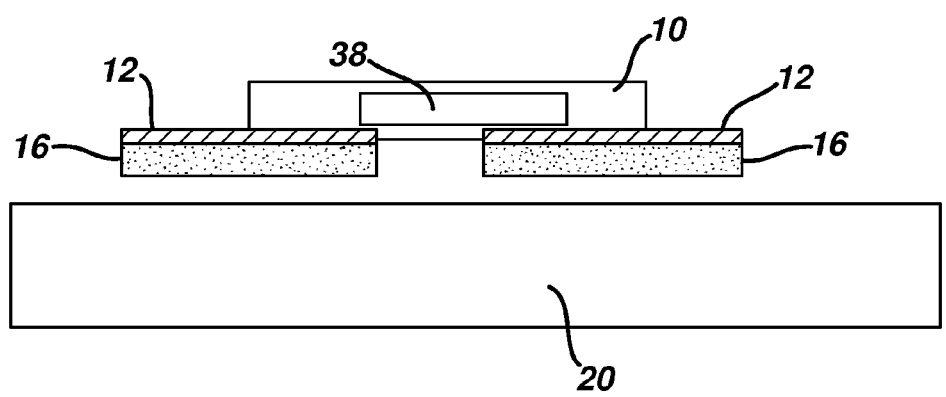
FIG. 3B illustrates an electrical sensory unit of the present invention.

Alternative therapeutic devices are shown in FIGS. 3A and 3B that rely upon an electric pulse or burst to provide the independent sensory cue. Electrode pads 12 can have optional carriers 16, such as a hydrogel coatings, that are positioned between electrode pads 12 and the exterior surface 20 of the body of the patient. The therapeutic device also includes a pulse generator 38 that is preferentially contained within housing 10. Electrode pads 12 and pulse generator 38 are connected via conductive lines 14. FIG. 3B illustrates an integrated or wireless embodiment of the present invention that uses an electric pulse or burst to provide the independent sensory cue.

In one embodiment, the sensory cue impulses are applied at a 10 microsecond duration and at above about 50V, but below about 130V. In another embodiment, the sensory cue impulses are applied at a 10 microsecond duration and at above about 50V, but below about 250 V. In another embodiment, the sensory cue impulses are applied at about a 50 microsecond duration and at about 30V. In yet another embodiment, the patient can adjust the voltage and/or pulse duration and/or frequency of pulses for sensory cue feedback for a desired sensation level.

The electric sensory cue impulses can be administered at time intervals of every 60 minutes, e.g. every 30 minutes, e.g. every 10 minutes, e.g. every 5 minutes, e.g. every 1 minute, e.g. every 30 seconds.

In one embodiment the electric sensory cue is applied using a pulse width of 1 micro-seconds to 10 milliseconds, e.g. from 10 micro-seconds to 1 millisecond.

In one embodiment the electric sensory cue is applied using a burst, which consists of a series of pulses that are separated by at least a discernible gap between each series of pulses.

In one embodiment the electrical sensory cue pulse is applied at a current density level above 0.2 milliAmps/cm$^2$ and below 0.4 milliAmps/cm$^2$.

In an embodiment of the current invention, the same electrodes that are used to deliver micro-current stimulation are also used to deliver the independent electrical sensory cue. Electric circuits capable of delivering two levels of voltages and currents are known to these skilled in the art. In one embodiment, a constant or pulsed micro-current is applied to the body of the patient continuously, while on a timed period, higher voltage is supplied to the same electrodes to deliver the independent sensory cue to the patient.

In another embodiment of the current invention, a separate pair of electrodes is used to deliver the independent electrical sensory cue. In yet another embodiment of the current invention, at least three electrodes are employed, with the first, common electrode used in both the micro-current circuit and in the electro-stimulated independent sensory cue circuit, while the second electrode is used only in the micro-current circuit, and the third electrode used in the independent electrical sensory cue circuit. In yet another embodiment of the current invention, a total of four electrodes are employed, with two electrodes used only in the micro-current circuit and two different electrodes used in the independent electrical sensory cue circuit.

In one embodiment, the pulse is raised in less than 5 microseconds, or less than 1 micro-second; and falls in less than 5 micro-seconds, or less than 1 micro-second. In one embodiment, a high current (e.g. 5-20 mA) short duration pulses are supplied through the same electrodes as the micro-current therapy (e.g. 20-50 microamp) current. The high current impulses are selected to result in a detectable sensation similar to TENS, but with much shorter or intermittently applied pulses, e.g. three 100 microsecond pulses at 100 Hz every 60 seconds or every 5 minutes. In this approach, the micro-current therapy device direct current voltage is superimposed with intermittent bursts of high voltage alternating current for sensory cue.

The electronic scheme for doing such combination of direct current stimulation and alternating current feedback is known to these skilled in the art. For example, a fly-back circuit can be used to generate the high voltage impulses (optionally discharged from a capacitor), which are then superimposed on the direct current signal which can be powered by the voltage taken directly from the battery. Optionally, the direct current signal can be interrupted when high current impulses are applied to the skin.

Figure 5:
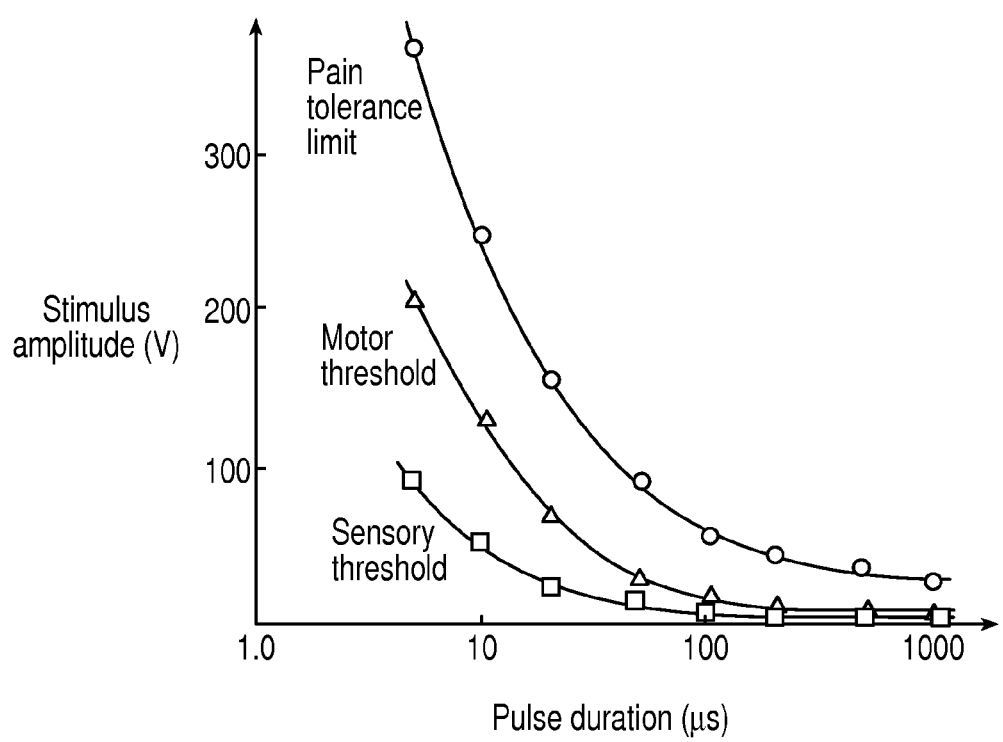
FIG. 5 is a correlation of sensory, motor and pain threshold as a function of voltage and pulse duration.

In one embodiment, the independent sensory cue is delivered through a separate electrical pulse, such as a current that is delivered at a voltage level at certain duration that can be sensed by the user. As shown in FIG. 5, an electrical pulse can be delivered at a stimulus amplitude voltage that is above the sensory threshold, but below the pain tolerance limit. So, while the microcurrent is delivered throughout the time in which the device is turned on, the sensed electrical pulse is felt intermittently to let the user know that the device is working. In one embodiment the pulse is delivered at the start of when the device is turned on, i.e. within the first 30 minutes, or within the first 15 minutes. In another embodiment the pulse is delivered at the start point and end point of the recommended treatment time, and the device has an optional integrated timer to let the user know when the treatment is completed by delivering the pulse. In one embodiment, the pulse is delivered above the sensory threshold but below the motor threshold at which the muscles contract. The pulse of electric current can be delivered through a separate circuit through electrode pads, with the option of adding a separate hydrogel layer onto the pads.

Sensate Cue Means

In one embodiment, a chemical agent is applied to the surface of the device that is applied to the skin. This chemical agent can be available as a fragrance, cooling agent, or heating agent to indicate to the consumer that the device is associated with pain relief. In one embodiment, the chemical agent is supplied as a topical analgesic in order to provide not only the sensory cue, but also immediate pain relief to accommodate the delay in relief that would be provided by the microcurrent therapy. The chemical agent may be added to the hydrogel, which is in turn added to the pad of the device, which is then applied to the skin. Optionally, there may be a separate pad or portion of the device which meters out the chemical agent at specified time intervals.

Figure 2A:
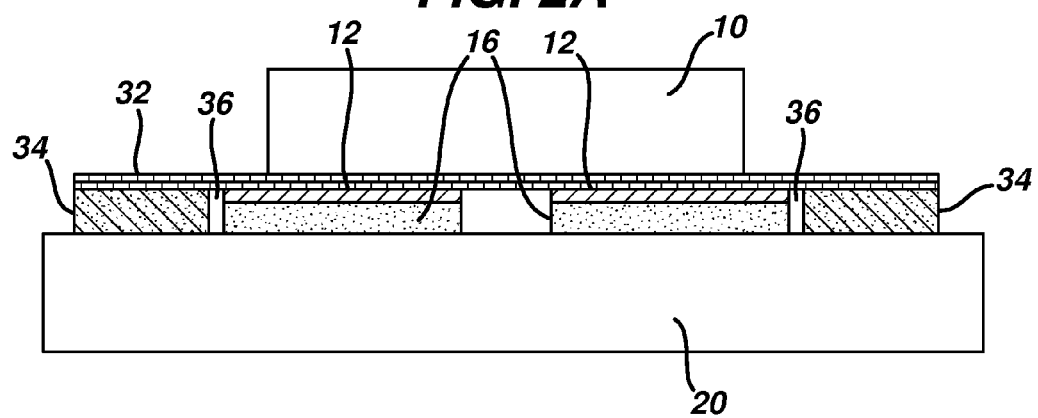
FIG. 2A illustrates a chemical sensory embodiment of the present invention.
Figure 2B:
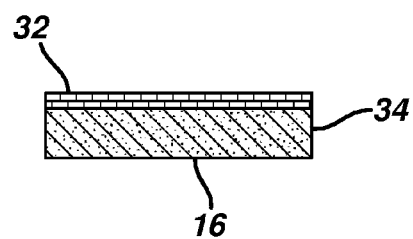
FIG. 2B illustrates a chemical sensory device of the present invention.

Referring to FIGS. 2A and 2B, an embodiment of an integrated or wireless electrostimulation device or micro-current therapy device is shown. Electrode pads 12 having optional hydrogel coating 16 are positioned on the exterior surface 20 of the body of the patient and are supported on a flexible support backing 32 in connection with the device body. Chemical sensates feedback or sensory cue means 34 are positioned in contact with the exterior surface 20 of the patient's body and are supported on a flexible support backing 32 in connection with the device housing 10. Chemical sensates feedback or sensory cue means 34 incorporate hydrogel or a coating, which can optionally be adhesive containing sensates. In one embodiment, there is a spacer or a gap 36 between chemical sensates sensory cue means 34 and electrode pads 12. In another embodiment, there is no gap or spacer between chemical sensates sensory cue means and electrode pads (not shown). In yet another embodiment, chemical sensates sensory cue means are incorporated into the hydrogel or other conductive coating on electrode pads (not shown).

Topical analgesics are a well known class of compounds and include but are not limited to counter irritants such as menthol, methyl salicylate, camphor, topical capsaicin, capsicum oleoresin; choline salicylate; ethyl salicylate; glycol salicylate; salicylic acid; turpentine oil; NSAIDs such as but not limited to diclofenac, felbinac, ibuprofen, ketoprofen, piroxicam, naproxen, and flurbiprofen; local anesthetics such as but not limited to lignocaine, lidocaine and benzocaine; and other active ingredients such as but not limited to including benzydamine, mucopolysaccharide polysulphate, salicylamide.

Examples of anti-inflammatory agent, include, but are not limited to, suitable steroidal anti-inflammatory agents such as corticosteroids such as hydrocortisone, hydroxyltriamcinolone alphamethyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclarolone acetonide, fludrocortisone, flumethasone pivalate, fluosinolone acetonide, fluocinonide, flucortine butylester, fluocortolone, fluprednidene(fluprednylidene)acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenalone acetonide, medrysone, amciafel, amcinafide, betamethasone, chlorprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylproprionate, hydrocortamate, meprednisone, paramethasone, prednisolone, prednisone, beclomethasone dipropionate, betamethasone dipropionate, triamcinolone, and salts are prodrugs thereof. The preferred steroidal anti-inflammatory for use in the present invention is hydrocortisone. A second class of anti-inflammatory agents which is useful in the compositions of the present invention includes the nonsteroidal anti-inflammatory agents.

In one embodiment a first chemical agent is added as a sensory cue and an additional second active chemical agent is added at a level at which a therapeutic amount of the agent is present to relieve pain.

Cooling agents may be sensates or chemicals which provide a sensory cooling effect on the skin, immediately or delayed, inhibit heat receptors or stimulate cooling receptors and include but are not limited to non volatile cooling agents, cooling sugars, cooling adjuvants, urea, polyvinyl alcohols, eucalyptus, polyacrylic acid, menthyl succinate, monomenthyl succinate, carboximides, acyclic carboximides, mannitol, p-menthane carboxamide, and peppermint oil.

"Cooling sugars", as described herein, shall include all sugar alcohols that have negative heats of solution (enthalpy, $\Delta H<0$ J/mol) and are known to impart some cooling sensation when placed upon the tongue of a user.

"Cooling adjutants", as described herein, shall refer to all compounds that have a negative heats of solution (i.e. an enthalpy, $\Delta H$ of less that $<0$ J/mol). Examples of suitable cooling adjutants include, but are not limited to cooling sugars.

Thermal Cue Means

Figure 4A:
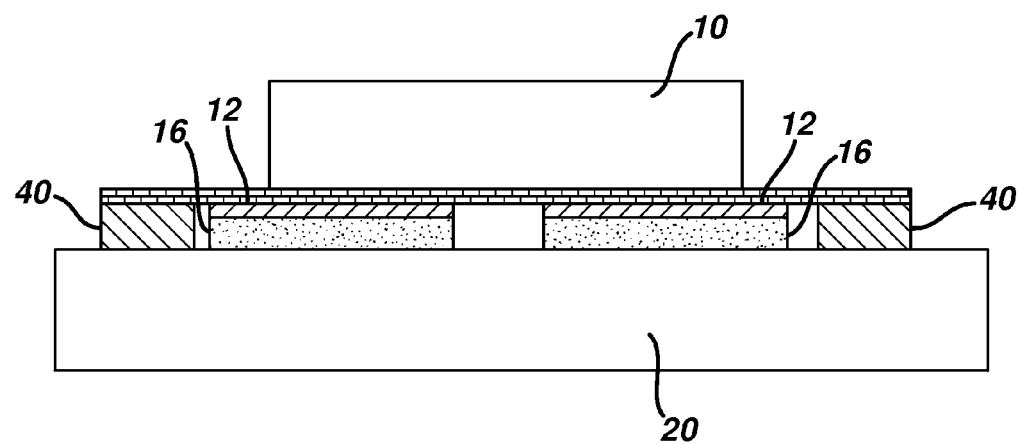
FIG. 4A illustrates alternative a warming sensory embodiment of the present invention.

In other embodiments of the device, there is provided a thermal sensory cue, as shown in FIG. 4A, whereby an electrically powered heating or cooling element provides periodic feedback to the user, with the user able to sense the thermal difference on user's skin. Electrode pads 12 can have optional carriers 16, such as a hydrogel coatings, that are positioned between electrode pads 12 and the exterior surface 20 of the body of the patient. The therapeutic device also includes at least one thermal sensory cue device 40 that is preferentially positioned in contact with surface 20 of a patient's skin. Electrode pads 12 are connected via conductive lines 14.

In one embodiment, a thermal sensory cue device is in direct or indirect contact with a user's skin and provides heating or cooling sensation. In one embodiment, every 3 minutes, every 5 minutes, or every 10 minutes, a short pulse of heating or cooling is provided as a sensory cue. In one embodiment the length of the pulse is 3 seconds, 10 seconds, or 1 minute. The heating or cooling is performed to vary the temperature on the skin by several degrees, in one embodiment by 3° C. to 10° C. The temperature changed is selected so as to provide a sensation of the sensory cue while simultaneously not to result in any overheating or overcooling of skin.

The heating is performed by electric heating element, such as electric resistive heating element. In one embodiment cooling is applied as a sensory cue utilizing Peltier devices. In one embodiment warming is applied as a sensory cue utilizing Peltier devices.

The thermal cue is provided by an electrically powered heating element or a cooling element or both. Electrically heated elements include resistively heated elements such as these consisting of conductive metallic traces on flexible supports, such as etched metallic traces. Other types of heaters include composite resistive heaters wherein conductive area is formed by substantially uniform coating of conductive paste or conductive coating, such as silver-powder plus non-conductive binder or carbon-powder plus non-conductive binder paste or coating. The conductive elements of the above heaters can be encapsulated between two layers of generally non-conductive materials or they can be supported on top of one substantially non-conductive supporting layer. Other types of resistively heated elements, include conductive ceramic elements, conductive tapes, insulated wire-based elements, and conductive coatings such as indium-tin oxide coating, and other types of heating elements. Thermo-electric elements, also known as Peltier elements, can also be utilized to provide heating or cooling sensory cue using electric power. Yet another type of element providing a thermal cue is based on a micro-fan element which is blowing ambient air on the skin. This element is utilizing cooling energy of ambient air to supply a cooling sensation and thus provide a thermal cue.

The circuit to power the electrically heated or cooled element includes a power supply, a current and/or voltage controller, as well as a timing circuit. Timing circuits, power supplies, and current and/or voltage controllers are widely available. Electric energy from the power supply is supplied to the electric heating or cooling element at pre-programmed times, controlled by the timing circuit. In one embodiment, the thermal cue is provided each 15 seconds, or each 30 seconds, or each 2 minutes, or each 5 minutes, or each 10 minutes, or at similar time intervals. In one embodiment, the heating or cooling is performed for 5 seconds, 10 seconds, 30 seconds, or 2 minutes or for similar time intervals. In one embodiment the heating or cooling is provided to change the temperature of the element by 5° C., 10° C., 15° C., or by 20° C., or by similar temperature increments, including either heating or cooling. The power supply used to power the electrically heated or cooled element in one embodiment can be the same power supply as used to power the microcurrent stimulation, or in one embodiment can be a separate power supply specifically designated to power the electrically heated or cooled element. A separate power supply dedicated to power the electrically heated or cooled element ensures that even when the thermal cue power supply is exhausted, the microcurrent treatment still continues powered by its own separate power supply.

In yet another embodiment, the thermal cue is provided by a heating pack, such as pack containing an iron-carbon-water exothermic powder mixture which is heated upon contact with air. In this embodiment the heating cue is provided constantly throughout the treatment or while the heating pack is active.

Timing Means

In one embodiment an internal clock exists in the device to control the delivery of the sensory cue. In the case of vibration, electrical pulses, ultrasound, LED generated heat or electrically generated heating or cooling the clock signals to the cue to turn itself on or off and for a specified period of time. In another embodiment the internal clock functions to time the physical release of a barrier, which in turn releases a chemical agent (warming, cooling, fragrance). In another embodiment the internal clock functions to time the physical release of a membrane or portions of a membrane, which allows for oxygen to permeate and begin an exothermic reaction, which in turn, generates heat. The clock's drift is less than approximately 1 minute per week.

Power Source Means

The device of the present invention includes a power source. The power source may be conventional direct current (DC) or pulsed DC, such as that disclosed in U.S. Pat. No. 5,042,975. In one embodiment, the current density (current intensity per unit area of the barrier membrane) to be used by the device in the present invention is generally less than about 0.5 mA/cm$^2$, such as less than about 0.1 mA/cm$^2$ or less than about 0.05 mA/cm$^2$. In one embodiment, the power source produces a voltage of from about 0.1 volts to about 9 volts, such as from about 1 to about 3 volts, such as about 1.5 volts. In another embodiment, the power source is connected to a voltage boosting/current regulating circuit that is capable of supplying a voltage up to 50 volts in order to provide a constant current output for the device.

In one embodiment, the power source is a battery (e. g., a rechargeable or disposable battery). In one embodiment, the battery is a disposable battery of small size suitable for a wearable patch or facial mask type adhesive device. Examples of suitable batteries include, but not limited to, button or coin batteries such as silver oxide, lithium, and zinc air batteries (which are typically used in small electronic devices). A zinc air battery is preferred because of its small size and high energy density, as well as its environmental friendliness. Examples of zinc air batteries include, but are not limited to, Energizer® AC5 and AC10/230 (Eveready Battery Co. Inc., St. Louis, Mo.) or their equivalents. Another preferred battery for the device is a flexible thin layer open liquid state electrochemical cell battery, such as a battery described in U.S. Pat. No. 5,897,522 and published U.S. Patent Application No. 2003/0059673A1. In another embodiment, the power source is a rechargeable battery, such as a Ni—Cd, Ni-MH, or Li-Ion rechargeable battery well known in the art. In another embodiment, the power source is a rechargeable supercapacitor, such as described in U.S. Pat. Nos. 6,552,895 and 6,275,372.

In another embodiment, the device is reuseable. For example, the device may comprise a re-useable part (e.g., a power source and electrodes) and a disposable part (e.g., the reservoir, electrodes and/or carrier). In one embodiment, the power source is a plug-in type of source.

In one embodiment of the device configuration, the microcurrent is delivered through two separate electrodes in contact with the patient's skin. In one embodiment of the device configuration, the two conductive electrodes are in ionic communication with the carrier containing an electrolyte (e. g., ions of one or more electrolytes in the carrier are in contact with the conductive electrode) and the carrier is in ionic communication with the skin. This electrode configuration differs from those in conventional iontophoresis devices in which each conductive electrode is in contact with a separate carrier (e.g., each electrode is contained in a separate compartment and affixed to the skin with electric insulation between them in order that all the electric current travels through the skin to complete the electric circuit). One advantage of this configuration is that the devices can be more versatile in its shape, thus increasing significantly their utility.

Galvanic Couple

In one embodiment, the device/composition of the present invention has a galvanic couple as its power source, wherein the electrons that pass between the first conductive electrode and the second conductive electrode are generated as a result of the difference of the standard potentials between the electrodes (e.g., the electricity is not generated by an external battery or other power source such as an AC power source).

Examples of such galvanic couples include, but are not limited to, zinc-copper, zinc-copper/copper halide, zinc-copper/copper oxide, magnesium-copper, magnesium-copper/copper halide, zinc-silver, zinc-silver/silver oxide, zinc-silver/silver halide, zinc-silver/silver chloride, zinc-silver/silver bromide, zinc-silver/silver iodide, zinc-silver/silver fluoride, zinc-gold, magnesium-gold, aluminum-gold, magnesium-silver, magnesium-silver/silver oxide, magnesium-silver/silver halide, magnesium-silver/silver chloride, magnesium-silver/silver bromide, magnesium-silver/silver iodide, magnesium-silver/silver fluoride, magnesium-gold, aluminum-copper, aluminum-silver, aluminum-silver/silver oxide, aluminum-silver/silver halide, aluminum-silver/silver chloride, aluminum-silver/silver bromide, aluminum-silver/silver iodide, aluminum-silver/silver fluoride, copper-silver/silver halide, copper-silver/silver chloride, copper-silver/silver bromide, copper-silver/silver iodide, copper-silver/silver fluoride, iron-copper, iron-copper/copper oxide, iron-copper/copper halide, iron-silver, iron-silver/silver oxide, iron-silver/silver halide, iron-silver/silver chloride, iron-silver/silver bromide, iron-silver/silver iodide, iron-silver/silver fluoride, iron-gold, iron-conductive carbon, zinc-conductive carbon, copper-conductive carbon, magnesium-conductive carbon, and aluminum-carbon.

The materials which serve to make up the galvanic couple may also serve as the connecting lead wires as well as the conductive electrodes of the device, e.g., zinc as the conductive anode and silver/silver chloride as the conductive cathode or zinc as the conductive anode and copper as the conductive cathode. The metals serve as the galvanic couple and conductive electrodes may also be alloys. Non-limiting examples of the alloys include alloys of zinc, copper, aluminum, magnesium as anode materials, and alloys of silver, copper, gold as cathode materials.

In one embodiment, the conductive electrode may be made of metal/metal or metal/nonmetal composite (e.g., held together by polymeric binders). Non-limiting examples of such composite conductive electrodes include (i) electrodes made of powders or flakes of silver, silver chloride, optional conductive carbon, and polymeric binders (e.g., dried coating of conductive silver/silver chloride ink) and (ii) electrodes made of powders or flakes of zinc, optional conductive carbon, and polymeric binders (e.g., dried coating of conductive zinc ink).

In one embodiment, the materials that make up the galvanic couple have a standard potential difference equal to or greater than about 0.1 volts, such as greater than about 0.2 volts such as greater than about 0.5 volts. In one embodiment, the materials that make up the galvanic couple have a standard potential difference equal to or less than about 3 volts.

In one embodiment, the device or composition of the present invention generates and/or is capable of generating current into the barrier membrane (i.e., current density) of from about 1 nano-A/cm$^2$ to about 500 micro-A/cm$^2$ of electricity such as from about 100 nano-A/cm$^2$ to about 50 micro A/cm$^2$.

In one embodiment, one of the conductive electrodes is in the form of a metal sheet, a metal wire, or a metal coated on a substrate (e.g., a metal or non-metal substrate such as a polymer, natural or synthetic fiber or fabric), and the other conductive electrode is attached or deposited to the other conductive electrode by means known in the arts, including, but not limited to, electroplating, electroless plating, binding with binders (e.g., conductive inks), plasma deposition, and combination thereof. In a further embodiment, the metal sheet is perforated. In one embodiment, such perforated metal sheet is in the form of a mesh such as a mesh of zinc, magnesium, aluminum, copper, or their alloys thereof.

In one embodiment, the second conductive electrode is in the form a fabric coated with a metal, and its oxide, halide, and sulfide, such as a fabric coated with silver, silver/silver oxide, silver/silver halide, zinc, magnesium, copper, copper/copper halide, copper/copper oxide. In another embodiment, the second conductive electrode is deposited to the first conductive electrode by chemical or electrochemical deposition such as electroless plating for chemical deposition and electroplating for electrochemical deposition as known in the art. In a further embodiment, the second conductive electrode is deposited to the first conductive electrode by physical deposition, such as spray coating, plasma coating, conductive ink coating, screen printing, dip coating, or vacuum deposition.

Carrier

Carrier 16 is an optional part of the present invention that facilitates the flow of current into and adhesion to the skin. Carriers 16 of the present invention can be a liquid (e. g., a solution, a suspension, or an emulsion which may be immobilized within an absorbent material such as gauze or nonwoven pad), a semi-solid (e.g., a gel, a cream, a lotion, microemulsion, or hydrogel), or a solid (e.g., a lyophilized composition containing active agents, which may be reconstituted by adding a liquid prior to use) that during use is capable of conducting electricity from a conducting electrode (e.g., the carrier contains one or more electrolytes, organic solvents, and water). In one embodiment, a chemical sensory cue is incorporated into the carrier.

In one embodiment, the carrier (e.g., a liquid or semi-solid) is added to the device by the user prior to applying the device to the barrier membrane. For example, the carrier is added to a reservoir in the device such that upon addition into the reservoir, both the conductive electrodes (e.g., the anode and the cathode) are in ionic communication with the carrier (e.g., the conductive electrodes are within or in contact with the reservoir). In one embodiment, the reservoir is a chamber containing the electrodes or an absorbent material that can immobilize the carrier (such as gauze or non-woven pad) that contains or is in contact with the electrodes (e.g., the electrodes are contained within or affixed to the absorbent material.

In one embodiment, the carrier is manufactured and placed in storage as a stable nonconductive composition (e.g., an anhydrous composition with negligible conductive ions). Prior to or during the use, as an activation step, water is mixed into the anhydrous composition to significantly increase its conductivity by enabling the passage of an electric current through the system. Examples of the carrier include, but are not limited to, skin creams, lotions, shampoos, moisturizers, skin toners, and cleansers. Other examples of carriers include biological fluids or excretion such as sweat, skin moisture, interstitial fluid, intercellular fluid, intracellular fluid, wound exudates, blood, saliva, menstrual fluid, tears, urine, and vaginal fluid that exit the body and enter into the reservoir of the device.

Examples of electrolytes include, but are not limited to, pharmaceutically acceptable organic and organic acids, bases, salts, buffers, peptides, polypeptides, proteins, nucleic acids, and/or other inorganic and organic compounds. Examples of salts include, but are not limited to, chloride salts (such as sodium chloride, potassium chloride, lithium chloride, calcium chloride, strontium chloride, magnesium chloride or other chloride salts), as well as salts of sodium, potassium, lithium, calcium, magnesium, strontium, fluoride, iodide, bromide. Examples of buffers include, but are not limited to, phosphates, citrates, acetates, lactates, and borates.

In one embodiment, the carrier contains a cooling, heating, fragrance sensate or combination thereof to be used as a sensory cue. In one embodiment, the carrier contains a warming agent, cooling agent, topical analgesic or combination thereof in a therapeutically effective amount to immediately relive pain.

In one embodiment, menthol is used at a level of about 2 percent to about 40 percent of the carrier, e.g. at a level of about 5 percent to about 30 percent of the carrier. In one embodiment methyl salicylate is used at a level of about 5 percent to about 60 percent of the carrier, e.g. at a level of about 10 percent to about 40 percent of the carrier. In one embodiment, the carrier comprises a skin penetration enhancer such as Quadrol™ or Neutrol™.

Electrodes

The conductive electrodes of the present invention may be reactive conductive electrodes or inert conductive electrodes. A "reactive conductive electrode" means a conductive electrode that goes through a change in its chemical composition as a result of electrode chemical reactions occurring when electric current passes through the electrode. In one embodiment, the reactive conductive electrode is an anode made of reactive materials such as a pure metal or a metal alloy including, but not limited to, zinc, aluminum, copper, magnesium, manganese, silver, titanium, tin, iron, and alloys thereof. The materials, which can serve as the galvanic couple described earlier, may also serve as the reactive conductive electrode. Upon passage of an electric current, metal ions such as zinc, copper, magnesium, manganese and/or aluminum cations are released from the anode into the carrier and delivered into the barrier membrane. Such ions may serve therapeutic benefits such as anti-microbial effects, immunologic modulation, enzymatic regulation, and/or anti-inflammatory effects.

In one embodiment, the reactive conductive electrode is made of reactive materials such as metal halides (e.g., silver-silver chloride (Ag/AgCl), silver-silver bromide, and silver-silver iodide). In this case, the primary electrochemical reaction at the cathode surface is conversion of solid silver halide to metallic silver with little unwanted consumption of the oxidizing agents generated by the anode. The released halide ions may be subsequently oxidized to oxidizing agents, such as chloride ions to chlorine ($Cl_2$), hypochlorous acid (HClO), and hypochlorite ions ($ClO^-$), and iodide ions to iodine.

An "inert conductive electrode" means a conductive electrode that does not go through a change in its chemical composition. In one embodiment, the anode is made of an inert conductive electrode, so that the electrochemical process at the surface of the anode generates oxidizing agents such as nascent oxygen (e.g., by electrolysis of water) and/or chlorine-containing oxidizing agents such as chlorine, hypochlorite, chlorate and perchlorate, and chlorine dioxide. Nascent oxygen is an oxidizing agent that is inhibitive to *P. acnes*, and chlorine-containing oxidizing agents are potent antimicrobial agent with bacteriacidal activity.

In one embodiment, the conductive electrode is made of, or coated on the surface of, an inert materials such as noble metals (e.g., gold, platinum, or gold-coated conductive metals), conductive carbon (e.g., glassy carbon or graphite), carbon-embedded polymers (e.g., carbon silicone rubbers), conductive carbon polymer foam or sponge, silver halide-coated silver (e.g., silver chloride-coated silver, silver bromide-coated silver, and silver iodide-coated silver), or corrosive resistant alloys. In another embodiment, a conductive electrode is in the form of a metal sheet, a metal wire, or a metal coated on a metal or nonmetal substrate (e.g., a polymer, natural or synthetic fiber or fabric), or is made by attaching or depositing a conductive electrode material to conductive or nonconductive substrate of a desired size and shape, such as by electroplating, electroless plating, binding with binders (e.g., conductive inks), plasma deposition, spray coating, plasma coating, conductive ink coating, screen printing, dip coating, or vacuum deposition, and combinations thereof.

In one embodiment, the anode of the device, serving as the conductive electrode, is made of aforementioned reactive conductive oxidizable metals such as zinc, calcium, magnesium, aluminum, iron, tin, copper, or alloys thereof, while the cathode, also serving as the conductive electrode, is made of the aforementioned reactive reducible conductive materials such as a more chemically stable metal and its metal halides, oxide, sulfide or other metal salts, such as silver and silver halides (e.g., silver chloride, silver bromide, silver iodide, silver fluoride), silver oxide, silver sulfide. In one embodiment, the reducible conductive material is in direct contact with a good electric conductor, such as: a thin layer of silver chloride, silver oxide, or silver sulfide over metallic silver; silver chloride powder with a binder (e.g., silver chloride ink); and/or silver chloride powder mixed with silver or conductive carbon powder held together by a binder in a matrix form (e.g., silver-silver chloride ink and silver chloride-carbon ink).

In another embodiment, the anode of the device in the present invention is made of aforementioned reactive conductive oxidizable metals while the cathode is made of aforementioned more chemically stable electrode materials such as conductive carbon, metallic silver, gold or platinum, or a powder mixture of conductive carbon and the noble metal in a matrix form as disclosed in U.S. Pat. No. 5,162,043.

In one embodiment, the ratio of the conductance measured between the first conductive and second conductive electrode of (i) the carrier and (ii) the skin hydrated with such carrier (wherein substantially all of the current passes between the electrodes through the skin) is in a range from about 10000:1 to about 1:100. In other words, the electric current distribution between $I_{carrier}$ and $I_{skin}$ is such that the value of $I_{carrier}/I_{skin}$ is between about 10,000 and about 0.01. $I_{carrier}$ is the portion of the total current going through the device ($I_{total}$) that only passes through the carrier layer between the anode and cathode without traveling through the skin, whereas $I_{skin}$ is the portion of $I_{total}$ that passes through the skin, namely, $I_{total}=I_{carrier}+I_{skin}$.

Decreasing the ratio of the conductance of the carrier relative to the conductance of the skin will result in a greater percentage of current passage through the skin, thereby enhancing iontophoretic delivery of any active agents being so delivered into the skin. Decreasing the conductivity of the carrier can nonexclusively be accomplished by adding less conductive materials to the carrier. Examples of such less conductive materials include, but are not limited to, oils such as silicone or hydrocarbon oils, air pockets such as air bubbles or air pockets in a semi-solid carrier, or polymer or clay beads. In one embodiment where the primary intention is to electrochemically generate species in the carrier, the value of $I_{carrier}/I_{skin}$ is between about 10,000 and about 1. In another embodiment, where the primary intention is to deliver electricity and/or active agents into the skin, the value of $I_{carrier}/I_{skin}$ is between about 10 and about 0.01. Adjustment of the value of $I_{carrier}/I_{skin}$ for a particular application can also be achieved by changing the distance between the first and the second electrode, or the distance between the two conductive electrode and the skin. For example, as the distance between the two conductive electrode decreases, the conductance measured between the two electrode increases and so is the $I_{carrier}$, leading to a increased value of $I_{carrier}/I_{skin}$. On the other hand, if the distance between the two conductive electrodes and the skin increases, the $I_{skin}$ increases, leading to decreased value of $I_{carrier}/I_{skin}$.

Light Therapy Means

In one embodiment, the device contains one or more light emitting diodes that can function to provide light therapy for treatment of various conditions or effect delivery of active agents. Light emitting diodes (LEDs) of certain spectrum may be incorporated into the device to emit light to the barrier membrane (e.g., to treat skin conditions such as acne and rosacea). The light emitting diode may also provide a signal to the user indicating that the device is operating properly.

In one embodiment, the LED emits light periodically (i.e., a blinking LED). In a further embodiment, such LED also modulates the current passing through the barrier membrane to form a pulsatile DC current. Such pulsatile DC current can enhance delivery of active agents into the barrier membrane, stimulate biological responses in the barrier membrane such as enhancing wound healing (e.g., in acne lesions), and/or enhanced skin sensation which serves a signal to a user that the device is working. Another potential advantage of using a blinking LED is to produce pulsatile DC current without the need of a complex electric circuit.

The spectrum of the LED's according to the current invention may range from about 300 nm to about 1500 nm, such as from about 350 nm to about 1000 nm. In one embodiment, the range of the LED includes violet-blue, green, red, and infrared ranges, e.g., from about 400 nm to about 450 nm such as from about 407 nm to about 420 nm; from about 510 nm to about 550 nm; from about 600 nm to about 700 nm; and from about 1300 nm to about 1500 nm. In one embodiment, the device contains two LEDs, one that emits light having a wavelength of from about 400 nm to about 500 nm and one which emits light from about 700 nm to about 1000 nm. Photosensitizer agents, such as 5-aminolaevulinic acid (ALA), hypericin, St. John's wort powder or extract, or other synthetic or natural photosensitizer agents, may be incorporated into the carrier as active agents to be delivered and irradiated by the device with LED's of the present invention.

The light irradiation from the LED's, together with the photosensitizer agent(s) and other aforementioned active agents, electrochemically generated oxidizing agents (e.g., peroxides, nascent oxygen, chlorine dioxide, and chlorine), and/or electric stimulation of the barrier membrane may work synergistically to achieve an improved efficacy in treating membrane disorders such as acne and rosacea. In one embodiment the LED functions in the infrared range, and subsequently provides heat, which functions as the sensory cue described herein.

Shape

The device can include a housing (not shown) that can be fabricated into various shapes and sizes to fit the contours of various anatomical surfaces of the barrier membranes. For example, the housing can be in the shape of a whole facial mask with openings/holes to expose the eyes, eye bows, nose, and mouth; a partial facial mask covering only the upper or lower half of the face; or a patch covering only the forehead, or the under eye region, the chin and jaw region, the neck, the back, wound, acne lesion or pimple, or other specific area of a barrier membrane in need of treatment. In another embodiment the device is shape is a flat patch applied to any area of the body, for example to the lower back.

In one embodiment the device conforms to a body part such as a hand, foot, knee, joint, elbow, neck and comprises any shape of a garment such as a glove, sock, mask, knee brace, elbow brace, or shirt. In one embodiment the device which is designed in the shape of a body part is made up of conductive fibers which deliver the microcurrent. In one embodiment, the conductive fibers may be used to deliver electrical heat.

Fabrication Materials

In one embodiment of the present invention, the housing is a water-insoluble substrate containing a galvanic couple, for example, a fine zinc wire or a fine zinc-coated fiber (e.g., zinc-coated polymer fiber) connected to a fine copper wire or a fine copper-coated fiber (e.g., copper-coated polymer fiber). One or more such fine galvanic couple wire(s) or fiber(s) may be incorporated into the substrate to create a device which, when in contact with the carrier (such as tap water or a liquid or semi-liquid composition including active agents) generates an electric current. In one embodiment, a galvanic couple-containing substrate may be made of multiple layer, for example, a layer of the zinc-containing substrate (e.g., a fine zinc wire- or a fine zinc-coated fiber in a woven or non-woven fabric) over a layer of copper-containing substrate (e.g., a fine copper wire- or a fine copper-coated fiber in a woven or non-woven fabric). During use, the layers contact each other to form the galvanic couple. In a further embodiment, the device releases beneficial ions (e.g., zinc ions or aluminum ions) that are delivered to the barrier membrane (e.g., the skin) when such a substrate is applied by the user (e.g., used as a wipe for cleaning the skin or a facial patch or mask to treat the skin). Active agents may also be incorporated into the substrate during manufacturing processes or be subsequently applied to the substrate prior to the application to the barrier membrane (e.g., in the form of an electrolyte or active agent containing liquid spray to wet the substrate). In one embodiment, the fabric is used as a dry wipe or a dry full or partial facial mask, to be wetted immediately before use, by applying water to the dry wipe or facial mask to pre-moisturized skin (e. g., by washing with tap water).

"Water insoluble" means that the substrate, upon immersion in distilled water at 25° C., does not readily dissolve in or readily break apart. The water-insoluble substrate may, however, be disintegrated and/or dissolved slowly, i.e., over a period of several hours up to several days. A wide variety of materials can be used as the water-insoluble substrate. Examples of suitable substrates include, but are not limited to, non-woven substrates, woven substrates, hydro-entangled substrates, air entangled substrates, natural sponges, synthetic sponges, and polymeric netted meshes.

The water insoluble substrates may be flushable. As used herein, "flushable" means that the substrate will pass through at least 10 feet of waste pipe in two toilet flushes. The material may also be biodegradable.

In one embodiment, the substrates contain a non-woven material. "Non-woven" means that the substrate, or a layer of the substrate, is comprised of fibers that are not woven into a fabric, but rather are formed into a sheet, mat, or pad layer. The fibers can either be random (i.e., randomly aligned) or they can be carded (i.e., combed to be oriented in primarily one direction. Furthermore, the non-woven substrate can be composed of a combination of layers of random and carded fibers).

Non-woven substrates may be comprised of a variety of natural and/or synthetic materials. "Natural" means that the materials are derived from plants, animals, insects, or byproducts of plants, animals, and insects. "Synthetic" means that the materials are obtained primarily from various man-made materials or from natural materials, which have been further altered. Non-limiting examples of natural materials useful in the present invention are silk fibers, keratin fibers (such as wool fibers, camel hair fibers) and cellulosic fibers (such as wood pulp fibers, cotton fibers, hemp fibers, jute fibers, and flax fibers).

Examples of synthetic materials include, but are not limited to, those selected from the group containing acetate fibers, acrylic fibers, cellulose ester fibers, cotton fibers, modacrylic fibers, polyamide fibers, polyester fibers, polyolefin fibers, polyvinyl alcohol fibers, rayon fibers, polyurethane foam, and mixtures thereof.

Substrates made from one or more of the natural and synthetic materials useful in the present invention can be obtained from a wide variety of commercial sources such as Freudenberg & Co. (Durham, N.C. USA), BBA Nonwovens (Nashville, Tenn. USA), PGI Nonwovens (North Charleston, S.C. USA), Buckeye Technologies/Walkisoft (Memphis, Tenn. USA), and Fort James Corporation (Deerfield, Ill. USA).

Methods of making non-woven substrates are also well known in the art. Such methods include, but are not limited to, airlaying, water-laying, melt-blowing, spin-bonding, or carding processes. The resulting substrate, regardless of its method of production or composition, is then subjected to at least one of several types of bonding operations to anchor the individual fibers together to form a self-sustaining web. The non-woven substrate can be prepared by a variety of processes including hydro-entanglement, thermally bonding, and combinations of these processes. Moreover, the substrates can have a single layer or multiple layers. In addition, a multi-layered substrate can include film layer(s) (e.g., aperture or non-aperture film layers) and other non-fibrous materials.

Strength or firmness of the non-woven material may be a desirable attribute. This can be achieved, for example, by the addition of binding materials, such as wet strength resins, or the material may be made of polymer binder coatings, stable fibres, e.g. based on cotton, wool, linen and the like. Examples of wet strength resins include, but are not limited to, vinyl acetate-ethylene (VAE) and ethylene-vinyl chloride (EVCL) Airflex emulsions (Air Products, Lehigh, Pa.), Flexbond acrylic polymers (Air Products, Lehigh, Pa.), Rhoplex ST-954 acrylic binder (Rohm and Haas, Philadelphia, Pa.), and Ethylene-vinyl acetate (EVA) emulsion (DUR-O-SET® by National Starch Chemicals, Bridgewater, N.J.). The amount of binding material in the substrate may range from about 5% to about 20%, by weight, of the substrate.

Non-woven materials of increased strength can also be obtained by using the so-called spunlace or hydro-entanglement technique. In this technique, the individual fibers are twisted together so that an acceptable strength or firmness is obtained without the need to use binding materials. The advantage of the latter technique is the excellent softness of the non-woven material.

In one embodiment, the non-woven material is made of a superabsorbent polymer. For the purposes of the present invention, the term "superabsorbent polymer" refers to materials that are capable of absorbing and retaining at least about 10 times their weight in body fluids under a 0.5 psi pressure. The superabsorbent polymer particles of the invention may be inorganic or organic crosslinked hydrophilic polymers, such as polyvinyl alcohols, polyethylene oxides, crosslinked starches, guar gum, xanthan gum, and other material known to the art of absorbent article manufacture.

Additives may also be added in order to increase the softness of the substrates. Examples of such additives include, but are not limited to, polyols such as glycerol, propylene glycol and polyethylene glycol, phthalate derivatives, citric esters, surfactants such as polyoxyethylene (20) sorbitan esters, and acetylated monoglycerides.

Sensory attributes may also be incorporated to the insoluble non-woven substrates. Examples of such sensory attributes include, but are not limited to color, texture, pattern, and embossing.

In one embodiment, the carrier is present in at least about 50%, such as at least about 75%, by weight of the total weight of the water insoluble substrate prior to use. In another embodiment, (i) the liquid carrier is present in less than about 10%, such as less than about 1%, by weight of the total weight of the water insoluble substrate (for example, the device may not contain any carrier prior to use). In a further embodiment, the product contains instructions for the user to either (i) wet the substrate prior to application or (ii) wet the barrier membrane (e.g., the skin) with water and/or another liquid prior to application.

In certain embodiments, zinc mesh may be used to construct the device. Zinc mesh (or "expanded zinc" as common called in battery and anti-corrosion fields) may be prepared from a thin zinc foil with mechanical perforation and subsequent expansion into net-like patterns. The major advantages of a zinc mesh anode in the galvanic device of the present invention are its ability of forming and retaining the desirable wrap/patch shape by a user, stretching by a user toward any directions to form wrap/patch of desirable size; and being breathable.

It should be noted although the use of zinc mesh is described here as an example of electrode designs, other aforementioned materials suitable for galvanic couple formation and for conductive electrodes can also be made into a mesh or an expanded form to provide the same function.

Zinc mesh also has the ability to conform to the shape of the membrane surface (e.g., the shape of an knee, elbow, neck) by gently pressuring it, and to retain this shape. This capability makes it uniquely suitable for a knee brace or certain skin patches to better fit the contours of certain anatomic features of the joint (e.g., a elbow patch) or body areas. This unique feature also assists in better electric contact and may also reduce dependence on using adhesives to affix the device to the skin.

Topical Compositions Containing Galvanic Pairs

In one embodiment, the present invention features a topical composition containing a first conductive metal particulates (such as fine flakes, wires/fibers or metal-coated fibers) selected from zinc, aluminum, copper, and their alloys; and a second conductive metal particulates (such as fine flakes, wires/fibers or metal-coated fibers) selected from silver, copper, gold, and their alloys. The first and second metal particulates can be selected from aforementioned electrode materials to form galvanic couples. Upon contact, the first conductive metal and the second conductive metal form a galvanic pair, generate electric current, and electrochemically generate ions. In a further embodiment, the difference of the standard potentials of the first conductive metal and the second conductive metal is at least about 0.1 V, such as at least about 0.5 V. For example, upon contact with a first conductive metal that contains zinc (such as fine zinc wires, zinc flakes or polymer fibers coated with zinc) and a second conductive metal that contains silver (such as a fine silver wires/fibers, silver flakes, or polymer fibers coated with silver), the composition generates electric current and zinc ions within the topical composition.

In one embodiment, the present invention features a topical composition containing particulates comprising at least two dissimilar metals in electric communication with each other to form galvanic power source unit (e.g., powders or small particles capable of generating galvanic current when in contact with an electrolyte medium or solution). Non-limiting examples of such galvanic particulates are small zinc powder or zinc flakes partially coated with silver/silver chloride, partial zinc coating on a conductive substrate such as a silver or silver/silver chloride coated polymer fibers/particles and solid or hollow glass or ceramic beads. In one embodiment, during storage, such galvanic particulates are placed in a container free of water/electrolyte solutions, or in a nonconductive solvent/solution. Upon application, the galvanic particulates come into contact with conductive solutions (e.g., an aqueous composition containing electrolytes or a body fluid) to be activated for electricity generation, and are deposited on to the barrier membrane surface to deliver electric current and/or active agents into the barrier membrane.

In one embodiment, the longest dimension of such particulate is at least twice (e.g., at least five times) the shortest dimension of such particulate, thereby allowing the particulate to lay along its longer dimension on the barrier membrane.

The composition may additionally contain an active agent, such as an anti-acne agent (such as salicylic acid, benzoyl peroxide, retinoic acid and/or retinol). The topical composition containing the first metal and the second metal is preferably a semi-solid form (such as a gel, a hydrogel, a water-in-oil emulsion, an oil-in-water emulsion, a cream, a lotion, an ointment, a multi-emulsion, a liposome, and/or a microcapsule formulation), and may contain the aforementioned fluid suspending or fluid absorbing materials. The topical composition may be prepared as such that one of the conductive metal is formulated in a separate phase from other conductive metal, for example, the first conductive metal (e.g., zinc flakes) is formulated in the discontinuous oil phase of an oil-in-water emulsion (e.g., a cream), while the second conductive metal (e.g., silver flakes) is formulated in the continuous aqueous phase of the emulsion. The topical composition of the present invention may also further contain a humectant (such as glycerin, propylene glycol, polyethylene glycol, sorbitol and/or urea) and aforementioned electrolytes to maintain certain moisture level and conductivity of the skin.

In one embodiment, during storage of such a topical composition, the first conductive metal and the second conduct metal are suspended substantially apart in a semi-solid composition (e.g., are not in contact with each other). Upon application to the membrane (such as the skin or mucosa) and partial drying of the liquid carrier, the contact of the first conductive metal and the second conductive metals results in galvanic couple formation and generation of electric current and metal ions of the first conductive metal, which provides benefits to the membrane such as antimicrobial, anti-inflammation, wound healing, iontophoretic delivery of active agents, tissue stimulation, and/or sebum reduction.

In one embodiment, the wires/fibers, flakes of conductive metals, or polymer fibers coated with the conductive metals are fine enough that they can be suspended in the semi-solid compositions during storage. In a further embodiment, they are in elongated shapes. The advantages of elongated shapes of the conductive metals (e.g., fine wires/fibers, flakes and polymer fibers coated with the conductive metals) include a lower apparent density and, therefore, a better floating/suspending capability in the topical composition; a higher probability of connection with another conductive material when low concentrations of the conductive metals are used; and a wider and deeper range of the membrane tissue (e.g., the skin) that the galvanic current travels through and provides the benefits to.

In one embodiment, the first and second conductive metal particles are formulated into different compositions and are stored in separate compartments of a dual chamber dispensing package. For example, the less chemically stable (e.g., more oxidizable) zinc or its alloy particulates may be formulated in an anhydrous, essentially non-conductive composition with organic solvents such as polyethylene glycols, propylene glycol, glycerin, liquid silicone and/or alcohol, or other pharmaceutically-acceptable organic solvents. The more chemically stable (e.g., less oxidizable) silver and silver chloride particulates may be formulated in an aqueous composition. The active agents may be formulated into either composition depending on their chemical stability and solubility. In use, the compositions are dispensed from dual chamber package (e.g., dual chamber pump, tube, pouch, bottle, etc.) and mixed prior or during application to the skin to form galvanic couples in situ to generate galvanic current and to treat the skin conditions.

In another embodiment, the aforementioned galvanic couples are manufactured as particulates to be incorporated into topical compositions. The particulates may be of any shape, including but not limited to, spherical or non-spherical particles or elongated or flattened shapes (e.g., metal or metal-coated spheres, hollow metal or metal-coated spheres, short metal-coated fibers or fabrics, and flakes), regular shapes (e.g., metal crystals), and irregular shapes (e.g., aggregated spheres). In one embodiment, the particulates have an average particle size of from about 1 micrometer to about 2 centimeters. In one embodiment, the particulates have an average particle size of from about 1 micrometer to about 2 millimeters for non-elongated shapes. In another embodiment, the particulates with elongated shapes have an average particle size from about 10 micrometers to about 2 centimeters such as from about 100 micrometers to about 50 millimeters.

In one embodiment, a polymer fiber of about 100 micrometers to about 10 millimeters in length is partially coated with silver or silver-silver chloride on one end (or only on certain portions of the fiber), and zinc on the other end (or on the remaining portions). In another example, the polymer fiber is coated completely with the first conductive metal (e.g., silver-silver oxide or silver-silver chloride), and one end (or certain portions of the fiber) is coated with the second conductive metal (e.g., zinc or magnesium). Silver-coated polymer fibers manufactured by Noble Fiber Technologies, Inc. (Clarks Summit, Pa.) can be coated with zinc using methods such as conductive zinc ink printing, electroplating, electroless deposition, vacuum deposition, and spray coating. Alternatively, a metallic zinc or magnesium particulate (e.g., bead or thin wire) may be coated at one end or at certain portions) with silver-silver oxide or silver-silver chloride. Spherical or non-spherical particles with an average particle size ranging from about one micrometer to about 5 millimeters can be partially covered with the first and second conductive metal coatings in a similar fashion.

The coating methods for such first and second conductive metals in preparing the galvanic couples can be electroless deposition, electric plating, vacuum vapor deposition, arc spray, conductive metal ink, and other known metal coating methods commonly used in electronic and medical device manufacturing processes. The galvanic couple particulates are preferably stored in aforementioned anhydrous forms, e.g., as a dry powder or immobilized in a fabric with binding agents, or as an essentially anhydrous non-conducting organic solvent composition (e.g., dissolved in polyethylene glycols, propylene glycol, glycerin, liquid silicone, and/or alcohol). The galvanic particulates have great versatility in applications, and can be used in many consumer and medical products such as patches, bandages, masks, garments, cloths, socks, head caps, gloves, mittens, bed sheets (e.g., by immobilized into the carrier or fabric), spread-on facial mask composition (such as a paste, cream or gel), creams, lotions, gels, shampoos, cleansers, powders, or incorporated into personal and medical products such as toothbrushes, dental flosses, periodontal implants or inserts, orthodontic braces, buccal patches, ocular inserts or implants such as contact lenses, nasal implants or inserts, wound dressings, diapers, sanitary napkins, dry wipes, pre-moistened wipes (with aforementioned anhydrous solvents), tampons, and rectal and vaginal suppositories. The galvanic particulates may also be incorporated into transdermal drug delivery patches to enhance drug penetration into the skin by iontophoresis and to reduce skin irritation by electric stimulation and electrically generated beneficial ions such as zinc ions.

The invention claimed is:

1. A method of indicating to a user that a microcurrent device is functioning by delivering an independent sensory cue selected from the group consisting of vibration, heat, cool, tingling, irritation, prick and combinations thereof, each above a sensory threshold level, wherein said user receives said sensory cue without any action by said user, wherein the independent sensory cue is delivered through a separate electrical impulse.

2. A method of indicating to a user that a microcurrent device is present on a user's body by delivering an independent sensory cue selected from the group consisting of vibration, heat, cool, tingling, irritation, prick and combinations thereof, each above a sensory threshold level, wherein said user receives said sensory cue without any action by said user, wherein the independent sensory cue is delivered through a separate electrical impulse.

3. A method of indicating to a user that a microcurrent device is not functioning, comprising the step of: delivering an independent sensory cue selected from the group consisting of vibration, heat, cool, tingling, irritation, prick and combinations thereof, each above a sensory threshold level to indicate to the user that the microcurrent device is not functioning.

* * * * *